(12) United States Patent
Hoegerle et al.

(10) Patent No.: US 12,255,511 B2
(45) Date of Patent: Mar. 18, 2025

(54) MULTI-OPERATING-VOLTAGE MOTOR

(71) Applicant: Aesculap AG, Tuttlingen (DE)

(72) Inventors: Roland-Alois Hoegerle, Tuttlingen (DE); Juergen Barth, Denkingen (DE)

(73) Assignee: Aesculap AG, Tuttlingen (DE)

( * ) Notice: Subject to any disclaimer, the term of this patent is extended or adjusted under 35 U.S.C. 154(b) by 172 days.

(21) Appl. No.: 17/795,589

(22) PCT Filed: Jan. 22, 2021

(86) PCT No.: PCT/EP2021/051487
§ 371 (c)(1),
(2) Date: Jul. 27, 2022

(87) PCT Pub. No.: WO2021/151798
PCT Pub. Date: Aug. 5, 2021

(65) Prior Publication Data
US 2023/0080962 A1    Mar. 16, 2023

(30) Foreign Application Priority Data

Jan. 28, 2020 (DE) ..................... 10 2020 101 990.4

(51) Int. Cl.
*H02K 3/28* (2006.01)
*H02P 25/18* (2006.01)
(52) U.S. Cl.
CPC .............. *H02K 3/28* (2013.01); *H02P 25/18* (2013.01); *H02K 2213/09* (2013.01)
(58) Field of Classification Search
CPC ....... H02K 3/28; H02K 2213/09; H02P 25/18
See application file for complete search history.

(56) References Cited

U.S. PATENT DOCUMENTS 10,931,218 B2    2/2021  Walzel
2012/0262014 A1  10/2012 Katou et al.
(Continued)

FOREIGN PATENT DOCUMENTS

DE    102012007173 A1    10/2012
DE    102013009036 A1    12/2014
(Continued)

OTHER PUBLICATIONS

Search Report received in German Application No. 10 2020 101 990.4 dated Oct. 23, 2020, with translation, 12 pages.
(Continued)

*Primary Examiner* — Forrest M Phillips
(74) *Attorney, Agent, or Firm* — Christopher A. Rothe; CM Law

(57) ABSTRACT

An electric motor includes a motor winding interconnection for operating an electrosurgical instrument with exactly one motor platform that is designed to operate the motor at a first operating voltage and a second operating voltage different from the first operating voltage. The motor platform includes a circuit, preferably a delta circuit or a star circuit, formed in each case by three phases with a respective phase coil. At least one phase coil is formed from N>1 interconnected individual coils. At the first operating voltage, the N individual coils of each phase coil are connected in parallel. At the second operating voltage, the N individual coils of each phase coil are connected in series. At least one short-circuiting mechanism per phase coil switches over between the first and second operating voltage.

11 Claims, 5 Drawing Sheets

(56) References Cited

U.S. PATENT DOCUMENTS

| | | | |
|---|---|---|---|
| 2018/0256287 A1 | 9/2018 | Bosisio et al. | |
| 2019/0222082 A1 | 7/2019 | Witczak et al. | |
| 2020/0162009 A1* | 5/2020 | Hatakeyama | F25B 31/02 |
| 2022/0224270 A1* | 7/2022 | Sugimoto | H02P 25/18 |
| 2022/0337184 A1* | 10/2022 | Nishihama | H02P 25/188 |
| 2022/0345062 A1* | 10/2022 | Sykora | H02P 25/18 |
| 2023/0166379 A1* | 6/2023 | Suzuki | H02K 7/145 |
| | | | 310/50 |
| 2024/0107940 A1* | 4/2024 | Odaka | A01D 34/81 |

FOREIGN PATENT DOCUMENTS

| | | |
|---|---|---|
| DE | 102016218664 A1 | 3/2018 |
| EP | 1111757 A2 | 6/2001 |
| EP | 1450469 A2 | 8/2004 |
| EP | 2701879 B1 | 3/2014 |
| EP | 3400645 A1 | 11/2018 |
| EP | 3435540 A1 | 1/2019 |
| EP | 3534532 A1 | 9/2019 |
| JP | 2014517774 A | 7/2014 |
| JP | 2017121158 A | 7/2017 |
| JP | 2019126175 A | 7/2019 |
| WO | 2013155601 A1 | 10/2013 |
| WO | 2018213919 A1 | 11/2018 |

OTHER PUBLICATIONS

Search Report received in International Application No. PCT/EP2021/051487 dated May 11, 2021, with translation, 7 pages.
Written Opinion received in International Application No. PCT/EP2021/051487 dated Oct. 11, 2021, with translation, 17 pages.

* cited by examiner

MULTI-OPERATING-VOLTAGE MOTOR

CROSS-REFERENCE TO RELATED APPLICATIONS

This application is the United States national stage entry of International Application No. PCT/EP2021/051487, filed Jan. 22, 2021, and claims priority to German Application No. 10 2020 101 990.4, filed Jan. 28, 2020. The contents of International Application No. PCT/EP2021/051487 and German Application No. 10 2020 101 990.4 are incorporated by reference herein in their entireties.

FIELD

The present disclosure relates to an electric motor having a motor winding interconnection for operating an electrosurgical instrument having exactly one motor platform.

BACKGROUND

Electric motor systems for surgery can be divided into two drive classes or operating-voltage classes, respectively. In one of the two drive classes or operating-voltage classes, the systems are operated with a battery, and in the other one of the two drive classes or operating-voltage classes, the systems have a mains connection, which is connected to a (power) network to supply the electric motor and thus the connected/attached electrosurgical instrument. In this case, a system operated with a battery is supplied with a voltage of 9.6 volts to 14 volts and a system operated with a mains connection or a (power) network is supplied with a voltage of 36 volts to 48 volts.

Prior art is known in which a separate motor platform with approximately 12 volts is provided for a battery-powered system and a separate motor platform with approximately 36 volts is provided for a mains-powered system. By using two different motor platforms, it is not possible to operate the same surgical instrument flexibly with a battery or a mains connection.

For various reasons, the two operating-voltage classes need to be combined on a single motor platform. On the one hand, this has advantages in terms of production technology, costs and certification, and on the other hand it has advantages for the user.

In the already known prior art, the combination of the two motor platforms on a single motor platform has several disadvantages. In a first case, increasing the system's battery power to 36 volts would result in a high machine weight and machine volume. This is unacceptable for the user, as it makes precise working and working over a longer period of time much more difficult.

In a second case, in which the system is operated with a mains connection reduced to 12 volts, the result would be a very unfavorable motor configuration. In particular, a high-speed drive, i.e. a drive with a high speed of, for example, more than 80,000 revolutions per minute, would also be unacceptable for the user in the second case due to the associated high heat generation.

Furthermore, only a star-delta changeover is known from the prior art. Here, however, it is only achieved that the motor can be operated in two different speed and power ranges with the same operating voltage.

Thus, for example, DE 10 2013 009 036 A1 relates to a drive unit for a comminution device, which has a star/delta switchable motor, a drive converter for regulating or controlling a physical variable of the motor, and a control unit, wherein switching devices are provided in the drive unit, which enable the star/delta switching, wherein the selection of the position of the switching devices is made by the control unit, and wherein the control unit takes into account at least one variable detected in the drive unit for this purpose.

EP 3 400 645 A1 describes a changeover device which has at least one electrical switch and is configured to connect the motor windings as a star or delta depending on the switch position.

Furthermore, the Dahlander motor is known from the prior art. Here, too, by switching the winding from 'delta to double star', the motor can be operated in two different speed and power ranges with the same operating voltage. This means that the Dahlander motor is a circuit variant for switching between different speeds.

For this reason, two independent, different motor platforms are currently offered. Compared to a uniform motor platform, this is disadvantageous due to higher manufacturing effort, development effort, certification effort and higher costs as well as poorer usability for the user and higher effort for motor data acquisition, motor data evaluation and integration into the IomT ('Internet of medical things', i.e., medical devices and tools that are connected to corresponding IT systems via the Internet).

Furthermore, the variants known from the prior art can only operate the operating voltage ratios, i.e. the ratio between a battery-powered operating voltage to the mains-powered operating voltage after a switch between the two operating possibilities, 1:2 or $\sqrt{3}$.

SUMMARY

Accordingly, the object of the present invention is to eliminate or at least reduce the problems known from the prior art. In particular, the object of the present invention is to provide an electric motor with a uniform motor platform that runs smoothly and ideally both in battery operation and in mains operation.

In other words, the aim is to offer an electric motor that is ideally configured for both operating voltages and therefore runs equally well. The motor characteristics should be identical at both operating voltages so that a common certification strategy can be implemented for both operating-voltage classes. The dimensions as well as the handling of the motors by the user or operator should not show any negative effects.

An electric motor with a motor winding interconnection for operating an electrosurgical instrument has exactly one motor platform. This motor platform is provided and configured to operate the motor at a first operating voltage and at a second operating voltage different from the first operating voltage. Furthermore, a circuit is provided on the motor platform, preferably a delta connection or star connection, which is formed by three phases with one phase coil each, and at least one phase coil is formed by N>1 interconnected individual coils.

The above object is solved in that for a motor winding interconnection according to the preceding aspect, in the first operating voltage, the N individual coils of each phase coil are connected in parallel and in the second operating voltage, the N individual coils of each phase coil are connected in series, and switching between the two operating voltages is provided via at least one short-circuiting means per phase coil.

In other words, by simply short-circuiting different potentials, it is possible to operate the motor at different operating voltages while maintaining the same motor characteristics and the same characteristic values. Accordingly, it is provided to switch the connection of the N individual coils from a series connection to a parallel connection or from a parallel connection to a series connection, respectively, in such a way with the aid of at least one short-circuiting means, in order to obtain the correspondingly required first or second operating voltage for battery operation or mains operation.

This has the advantage that the motor platform is configured identically for both operating systems—battery operation and mains operation—and no critical elements such as switches, electronic components or the like are required to switch between battery operation and mains operation, or mains operation and battery operation, respectively. In addition, it is advantageous that the present invention functions equally well with both a star connection and a delta connection.

For example, an exemplary embodiment may be delta connected in the battery-powered system, with a wire diameter of preferably 0.355 mm. In this case, each phase coil consists of three individual coils connected in parallel, each with thirteen turns (a total of 39 turns per phase coil), and outputs 12 volts. In the corresponding mains-powered system, an exemplary embodiment is also delta connected with a wire diameter of preferably 0.355 mm and three individual coils with thirteen turns each (a total of 39 turns per phase coil) for each phase coil, which are each connected in series and output 36 volts.

It is preferred if each phase coil has N individual coils and the first operating voltage with preferably 12 V for operating the motor with a battery is in a ratio of 1:N to the second operating voltage with preferably 36 V for operating the motor via a mains connection. In particular, it is preferred if each phase coil has three individual coils and the first operating voltage to the second operating voltage are in a ratio of 1:3. Alternatively, it is preferred if each phase coil has two individual coils and the first operating voltage to the second operating voltage are in a ratio of 1:2. It is further preferred if each phase coil has four or more individual coils and the first operating voltage is in a ratio of 1:4, 1:5, etc. to the second operating voltage.

It is advantageous if the at least one short-circuiting means is configured as a passive component. This means that the technical implementation can be carried out in the simplest way by mounting a single passive component. Furthermore, the use of such a passive component has the advantage that it is also suitable for use in medical technology and can be subjected to appropriate cleaning, sterilization and reprocessing procedures.

It is furthermore preferred if the at least one short-circuiting means is mounted on a first insertion disk, with which the N individual coils are short-circuited or with which connections between the N individual coils are interrupted in such a way that the N individual coils are connected in parallel with each other in order to operate the motor at the first operating voltage. It is understandable that a multiple, preferably a double, of the number of individual coils is attached to short-circuiting means on the first insertion disk. In other words, according to a preferred embodiment, when switching from the second operating voltage to the first operating voltage, two short-circuiting means are used per phase, i.e. per three individual coils. In contrast, according to a preferred embodiment, only one short-circuiting means is used per phase coil, i.e. per three individual coils, when driving with the second operating voltage (if required).

It is advantageous if the at least one short-circuiting means is mounted on a second insertion disk, with which connections between the N individual coils are interrupted or with which the individual coils are short-circuited in such a way that the individual coils are connected in series with each other in order to operate the motor at the second operating voltage. It is understandable that a multiple, preferably a double, of the number of individual coils is attached to short-circuiting means on the second insertion disk.

Furthermore, it is preferred if the first insertion disk is provided and configured to be inserted between the motor and the battery. This has the advantage that the user only has to mechanically insert the first insertion disk in order to switch from mains operation to battery operation, i.e. to switch from preferably 36 volts to 12 volts operating voltage. Thus, the first insertion disk has to be interconnected to reach the respective lower operating voltage. This can be done by the user or the first insertion disk may already be integrated in the lower voltage supply. A motor that has previously only been used in mains operation can now be operated in battery mode without any further modifications or manipulations by the user. A mains (cable) drive can therefore also be operated with battery.

It is advantageous if the second insertion disk is provided and configured to be inserted between the motor and the mains connection. This has the advantage that the user only has to mechanically insert the second insertion disk in order to switch from battery operation to mains operation, i.e. to switch from preferably 12 volts to 36 volts operating voltage. Thus, the second insertion disk has to be interconnected to reach the respective higher operating voltage. This can be done by the user or the second insertion disk may already be integrated in the higher voltage supply. A motor that has previously only been used in battery operation can now be operated in mains operation without any further modifications or manipulations by the user. A battery drive can therefore also be operated with mains (cable).

It should be noted that depending on the motor winding interconnection, which consists of the three individual coils and which is integrated into the electric motor or is mounted on the side of the motor platform facing the electric motor, no insertion disk is used in mains operation. In the case that no insertion disk is used, the individual coils are already firmly connected in series with each other and with the insertion of an insertion disk via the short-circuiting means located on it, the series connection becomes a parallel connection and can finally be operated with a battery.

Alternatively, the three individual coils can be mounted on the motor platform in such a way that an insertion disk is already used for the series connection, which connects the individual coils accordingly via a short-circuiting means. This insertion disk is replaced when switching to battery operation.

Furthermore, depending on the specific constructive requirements of different motor types, it may not be sufficient to achieve the desired interconnection only by short-circuiting the low voltage variant. In this case, additional circuit interconnections of the higher operating voltage have to be interrupted. This is provided by the second insertion disk for the operation of the higher operating voltages.

It is furthermore advantageous if the motor platform has four output conductors per phase, which are directed towards the battery or the mains connection and can be plugged into the short-circuiting means.

Furthermore, it is advantageous if the circuitry that is taken over by the first insertion disk or the second insertion disk is activated or deactivated electronically by the respective connected motor controller. This would eliminate the need for manual insertion or removal of the first or respectively second insertion disk.

It is also preferred if the motor platform is provided and configured in such a way that the motor characteristics and the characteristic values of the motor are identical during operation in the first and second operating voltages, which are different from each other. This means that parameters such as the speed or torque are identical to each other both in battery operation and in mains operation.

Furthermore, the present invention relates to a motor platform which carries an entire motor winding interconnection for operating an electrosurgical instrument, comprising a circuit, preferably a delta connection or star connection, formed by three phases each having a phase coil, and at least one phase coil is formed from N>1 interconnected individual coils, wherein in the first operating voltage, the N individual coils of each phase coil are connected in parallel and in the second operating voltage, the N individual coils of each phase coil are connected in series, and switching between the first and second operating voltages is provided via at least one short-circuiting means per phase coil. It should be noted that the motor platform can be combined with the above aspects.

Furthermore, the present invention relates to a system comprising an electric motor and a motor winding interconnection according to one of the preceding aspects, wherein the electric motor is provided and adapted to be driven by two different voltage sources.

It is preferred if the first voltage source is an energy storage device, preferably a battery. The battery is formed by three battery cells which have a voltage of 3 to 4 volts to supply the motor to be driven with a total of 12±2 volts. The use of such an energy storage device is primarily for powering larger surgical instruments. The use of three battery cells has the advantage that they are not too large or too heavy for use in a surgical instrument and also have a voltage which is high enough to drive the motor with sufficient power. In addition, the time between two operations/applications is long enough to ensure charging of the energy storage device due to the indispensable reprocessing. Due to the size or the weight, an implementation with a higher voltage is not practical.

It is preferred if the second voltage source is a control device connected to the mains to supply the motor to be driven with a voltage of 36 to 39 volts. Here it is advantageous that the voltage supply is close to 40 volts, above which the standards for air and creepage currents would be increased. An increase in air and creepage currents, and thus a voltage of 40 volts or more, would at the same time mean a larger motor, making the surgical instrument heavier and more difficult to handle. This is particularly important in the operation of small bone surgery, such as brain/neurosurgery, etc., for the use of which the second voltage source is provided. The first voltage source described above is already too large and heavy for this use and would be in the operator's field of view when used. Furthermore, it is preferred if the voltage is as high as possible, since then the currents are smaller and thus thinner cables can be installed. Another advantage of the second voltage source near the 40 volts is the regulatory freedom below the 40 volts is greater than above. This means that higher voltages are more dangerous for patients and thus a voltage below the so-called 'protective voltage' is advantageous/easier to implement, in particular with regard to insulation.

Furthermore, it is preferred if the aforementioned system can be sterilized. Therefore, sufficient insulation is necessary, which is much easier to implement at voltages below 40 volts.

In summary, it is an object of the present invention to provide a motor winding interconnection which permits operation of a motor at two different operating voltages. However, the motor characteristics and mechanical output values remain unchanged at both operating voltages. Therefore, the same motor can be operated by either mains or battery with the same operational application.

BRIEF DESCRIPTION OF THE DRAWING FIGURES

In the figures, identical reference signs denote identical or at least equivalent parts and components. For practical purposes, multiple redundant descriptions of such parts and components are omitted.

DETAILED DESCRIPTION

The invention is explained in more detail below by means of a preferred embodiment with reference to the accompanying figures. For the sake of clarity, only one phase coil 7 has been replaced by the corresponding individual coils 8 in the figures.

Figure 1:
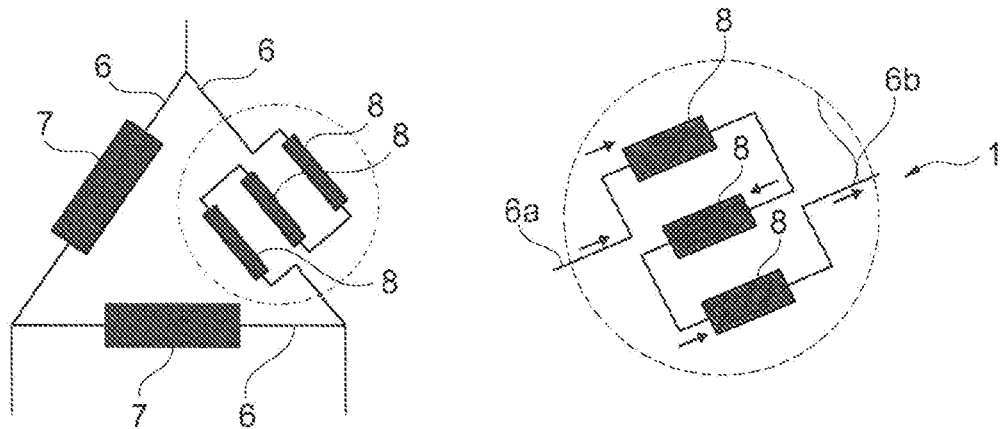
FIG. 1 is a representation of a motor winding interconnection in a delta connection with the second operating voltage.

FIG. 1 is a representation of a motor winding interconnection 1 in a delta connection with the second operating voltage 5. On the left side of FIG. 1, a delta connection known from the prior art can be seen. The delta connection consists of three phases 6, each with a phase coil 7. According to a preferred embodiment of the present invention, each of the three phase coils 7 is replaced by three individual coils 8.

The three individual coils 8 can be seen on the right side of FIG. 1. The three individual coils 8 are connected in series between a phase input 6a and a phase output 6b. The arrows on the right side of FIG. 1 indicate the direction of the current flow.

Such a motor winding interconnection 1 is provided for mains operation and has the following optimum configuration for the second operating voltage 5:

TABLE 1

| Magnetic flux | Φ = constant |
|---|---|
| Voltage | U (e.g. 36 volts) |
| Number of turns | N |
| Coil current | I |
| Wire cross section | A |
| Resistance | R |

Figure 2:
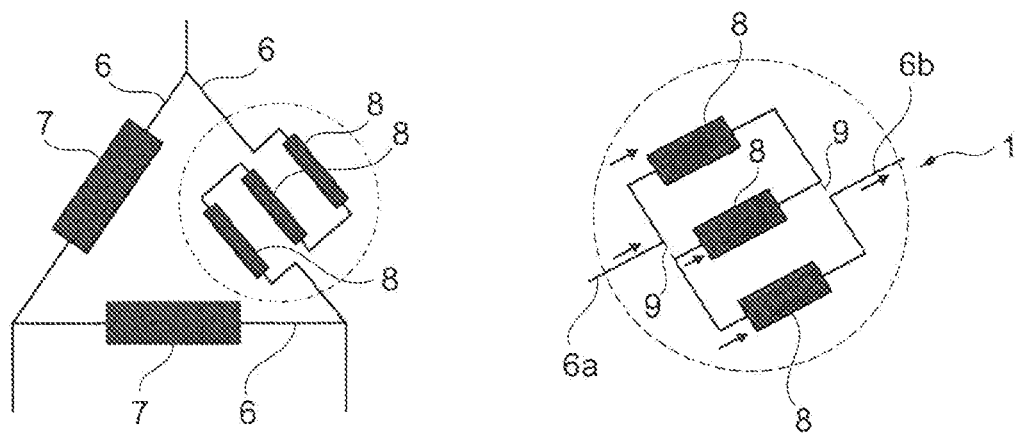
FIG. 2 is a representation of a motor winding interconnection in a delta connection with the first operating voltage.

FIG. 2 is a representation of a motor winding interconnection 1 as a delta connection with the first operating voltage 4. On the left side of FIG. 2, a delta connection known from the prior art can be seen. The delta connection consists of three phases 6, each with a phase coil 7. According to a preferred embodiment of the present invention, each of the three phase coils 7 is replaced by three individual coils 8.

The right side of FIG. 2 is almost identical to the right side of FIG. 1, with the difference that two short-circuiting means 9 short-circuit the three individual coils 8 connected in series in such a way that the three individual coils 8 are now connected in parallel between the phase input 6a and the phase output 6b. The arrows shown on the right side of FIG. 2 again indicate the direction of the current flow.

Such a motor winding interconnection 1 is provided for battery operation and has the following optimum configuration for the first operating voltage 4:

TABLE 2

| Magnetic flux | Φ = constant |
|---|---|
| Voltage | U/3 (e.g. 12 volts) |
| Number of turns | N/3 |
| Coil current | 3I |
| Wire cross section | 3A |
| Resistance | R/3 |

Figure 3:
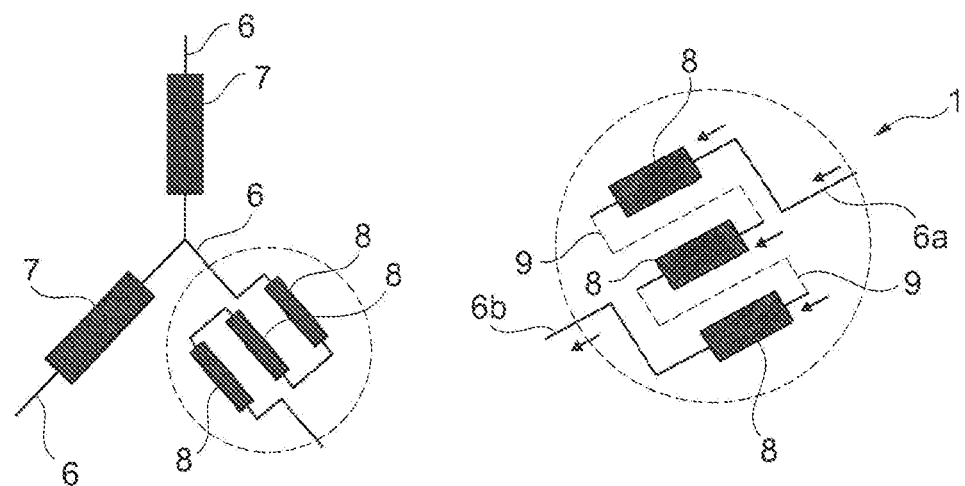
FIG. 3 is a representation of a motor winding interconnection in a star connection with the second operating voltage.

FIG. 3 is an illustration of a motor winding interconnection 1 as a star connection with the second operating voltage 5. On the left side of FIG. 3, a star connection known from the prior art can be seen. The star connection consists of three phases 6, each with a phase coil 7. According to a preferred embodiment of the present invention, each of the three phase coils 7 is replaced by three individual coils 8, as in FIG. 1.

The three individual coils 8 can be seen on the right side of FIG. 3. The three individual coils 8 are connected in series between the phase input 6a and the phase output 6b. The arrows on the right side of FIG. 3 indicate the direction of the current flow.

Such a motor winding interconnection 1 is provided for mains operation and has the same optimum configuration for the second operating voltage 5 according to preceding table 1. In contrast to the motor winding interconnection 1 according to FIG. 1, the motor winding interconnection 1 according to FIG. 3 already has two short-circuiting means 9 which enable the three individual coils 8 to be connected in series between the phase input 6a and the phase output 6b.

Figure 4:
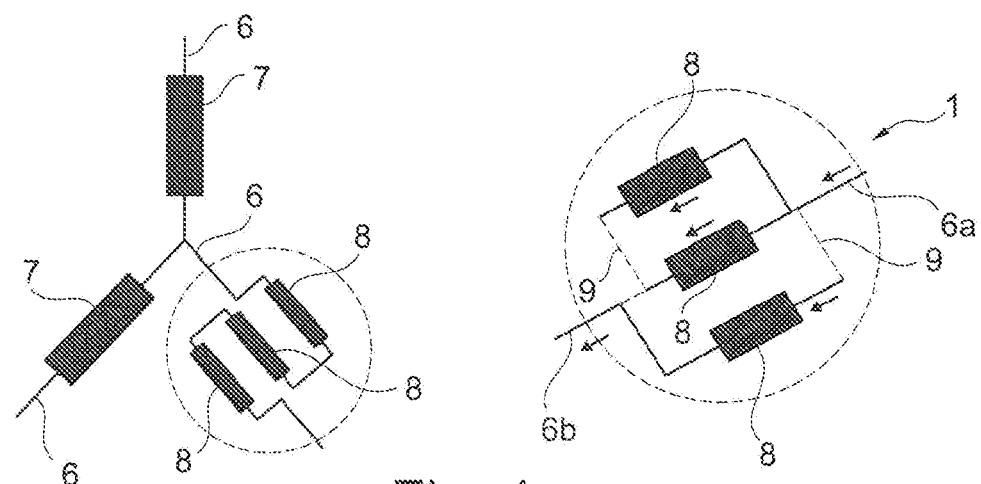
FIG. 4 is a representation of a motor winding interconnection in a star connection with the first operating voltage.

FIG. 4 is an illustration of a motor winding interconnection 1 as a star connection with the first operating voltage 4. On the left side of FIG. 4, a star connection known from the prior art can be seen. The star connection consists of three phases 6, each with a phase coil 7. According to a preferred embodiment of the present invention, each of the three phase coils 7 is replaced by three individual coils 8.

The right side of FIG. 4 corresponds almost completely to the right side of FIG. 3, with the difference that two short-circuiting means 9 short-circuit the three series-connected individual coils 8 in such a way that the three individual coils 8 are now connected in parallel between the phase input 6a and the phase output 6b. The arrows shown on the right side of FIG. 4 again indicate the direction of the current flow.

Such a motor winding interconnection 1 is provided for battery operation and has the same optimal configuration for the first operating voltage 4 according to preceding table 2 above. In contrast to the motor winding interconnection 1 according to FIG. 2, the motor winding interconnection 1 according to FIG. 4 has other short-circuiting means 9 which enable the three individual coils 8 to be connected in parallel with each other between the phase input 6a and the phase output 6b.

Based on these above configurations and the motor winding interconnections 1 when operating the electric motor 2 in the first operating voltage 4 according to FIGS. 2 and 4 or respectively in the second operating voltage 5 according to FIGS. 1 and 3, it is possible to obtain the same power characteristics for the first as well as for the second operating voltage 4 and 5. Therefore, according to the following formulas, the following relationship applies between the series connection according to FIG. 1 or 2 and the parallel connection according to FIG. 2 or 4:

$$U_{series}=U_1+U_2+U_3=3U(\triangleq 36 \text{ volts})$$

$$U_{paranel}=U_1=U_2=U_3=U(\triangleq 12 \text{ volts})$$

Thus, the ratio of the first operating voltage 4 to the second operating voltage 5 is one to three.

In an alternative embodiment, only two individual coils 8 can be used for each phase coil 7, with the result that the ratio of the first operating voltage 4 to the second operating voltage 5 is one to two. Accordingly, N>1 interconnected individual coils 8 can be used, resulting in a one to N ratio.

Figure 5:
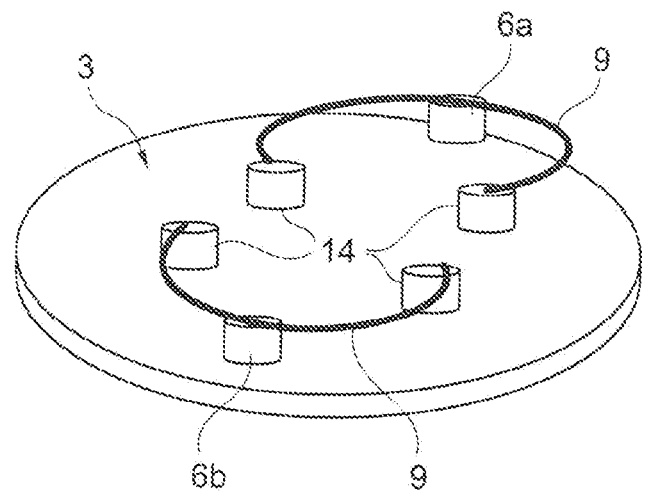
FIG. 5 is a simplified representation of a circuit according to FIG. 4 with two short-circuiting means 9 for the drive with a first operating voltage.

FIG. 5 is a simplified representation of a circuit according to FIG. 4 with two short-circuiting means 9 for the drive with a first operating voltage 4. FIG. 5 shows the motor platform 3, which is directed towards the battery 10 or the mains connection 11. Four output conductors 14 emerge from the motor platform 3. Two of the four output conductors 14 are short-circuited to each other via one of the two short-circuiting means 9 and connected to the phase input 6a. The other two of the four output conductors 14 are short-circuited to each other via the other short-circuiting means 9 and connected to the phase output 6b. All connections of the output conductor 14, which are not visible on the motor platform 3, are provided as fixed connections on the other side, as explained below for a preferred embodiment in FIG. 10.

Figure 6:
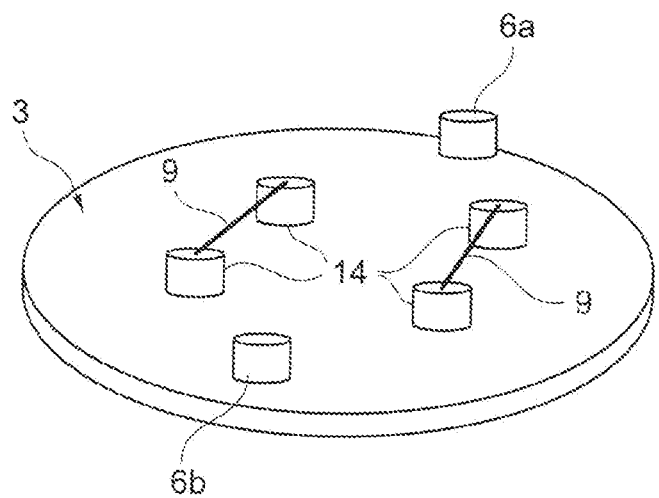
FIG. 6 is a simplified representation of a circuit according to FIG. 3 with two short-circuiting means 9 for the drive with a second operating voltage.

FIG. 6 is a simplified representation of a circuit according to FIG. 3 with two short-circuiting means 9 for the drive with a second operating voltage 5. FIG. 6 shows the motor platform 3, which is directed towards the battery 10 or the mains connection 11. Four output conductors 14 emerge from the motor platform 3. Two of the four output conductors 14 are short-circuited to each other via one of the two short-circuiting means 9. The other two of the four output conductors 14 are short-circuited to each other via the other short-circuiting means 9. All connections of the output conductor 14, which are not visible on the motor platform 3, are provided as fixed connections on the other side, as explained below for a preferred embodiment in FIG. 10.

Figure 7:
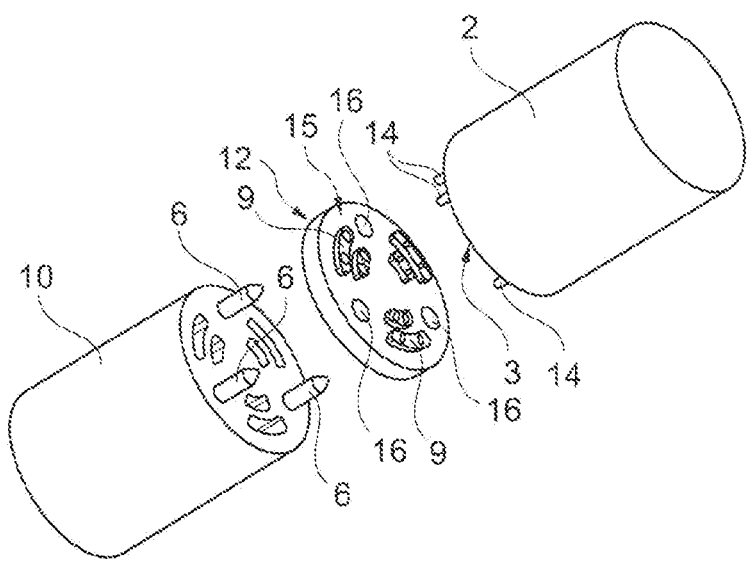
FIG. 7 is an exploded view of an electric motor with the first operating voltage and the first insertion disk.

FIG. 7 is an exploded view of an electric motor 2 with the first operating voltage and the first insertion disk 12. FIG. 7 shows the electric motor 2, the battery 10 and the first insertion disk 12. Three phases 6 emerge from the battery 10, which supply the electric motor 2 with power. The first insertion disk 12 is inserted between the electric motor 2 and the battery 10. The first insertion disk 12 has three phase holes 16. A phase 6 protruding from the battery 10 is inserted into each phase hole 16. On the motor support side 15, which is the side facing away from the battery 10, a plurality of short-circuiting means 9 are provided to short-circuit the individual coils 8 of FIGS. 2 and 4 together.

Figure 9:
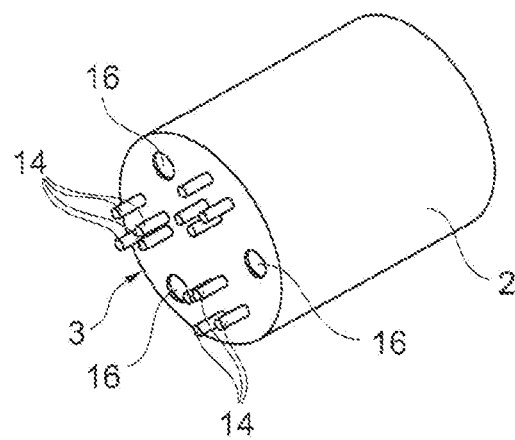
FIG. 9 is a representation of the electric motor and its motor platform.

The electric motor 2 also has three phase holes 16, as shown in FIG. 9, into which the phases 6 of the battery 10 are inserted. Four output conductors 14 emerge from the motor platform 3 of the electric motor 2 for each individual coil 8 integrated in the electric motor 2. The four output conductors 14 are short-circuited accordingly when the first insertion disk 12 is inserted between the electric motor 2 and the battery 10.

Figure 8:
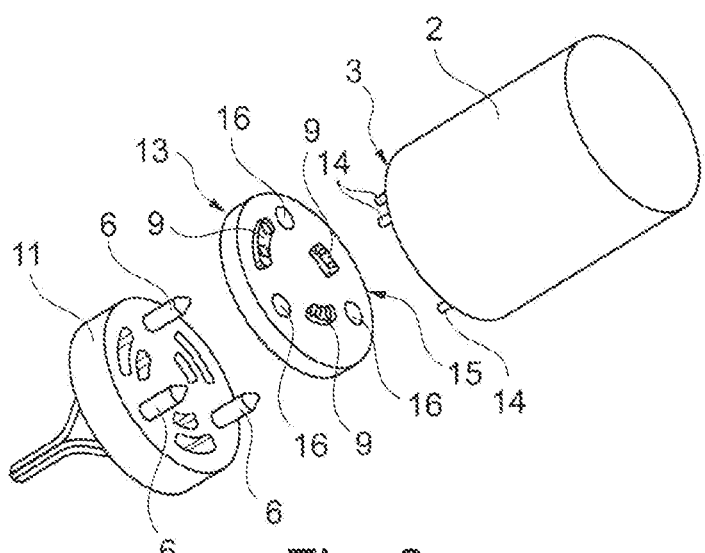
FIG. 8 is an exploded view of an electric motor with the second operating voltage and the second insertion disk.

FIG. 8 is an exploded view of an electric motor 2 with the second operating voltage and the second insertion disk 13. FIG. 8 shows the electric motor 2, the mains connection 11 and the second insertion disk 13. Three phases 6 emerge from the mains connection 11 and supply the electric motor 2 with power. The second insertion disk 13 is inserted between the electric motor 2 and the mains connection 11. The second insertion disk 13 has three phase holes 16. A phase 6 protruding from the mains connection 11 is inserted into each phase hole 16. On the motor support side 15, which is the side facing away from the mains connection 11, there are several short-circuiting means 9 which short-circuit the individual coils 8 from FIGS. 2 and 4 with each other.

As shown in FIG. 7, the electric motor 2 also has three phase holes 16, as shown in FIG. 9, into which the phases 6 of the mains connection 11 are inserted. Four output conductors 14 emerge from the motor platform 3 of the electric motor 2 for each individual coil 8 integrated in the electric motor 2. The four output conductors 14 are short-circuited accordingly when the second insertion disk 13 is inserted between the electric motor 2 and the mains connection 11.

FIG. 9 is a representation of the electric motor 2 and its motor platform 3. Four output conductors 14 emerge from the motor platform 3 for each individual coil 8 integrated in the electric motor 2. These are connected by inserting the first or second insertion disk 12 or 13 according to FIGS. 5 and 6 via short-circuiting means 9 (not shown). Thus, this motor platform can be used unchanged in the first operating mode 4 and in the second operating mode 5.

Figure 10:
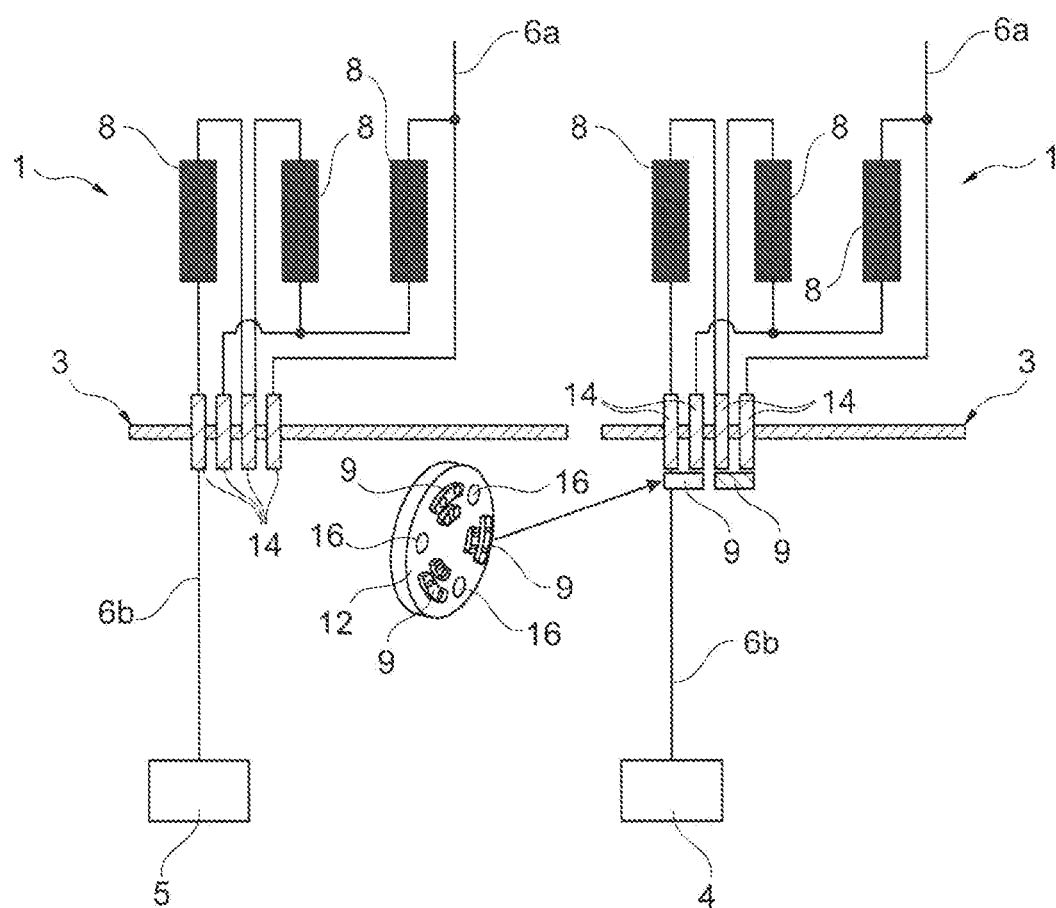
FIG. 10 is a representation of the motor winding interconnection of the three individual coils of a phase coil in mains operation and in battery operation.

FIG. 10 is a representation of the motor winding interconnection 1 of the three individual coils 8 of a phase coil 7 in the electric motor 2 with the first operating voltage 4 and the second operating voltage 5. FIG. 10 shows on the left side the motor winding interconnection 1 of the three individual coils 8 and their connection to the respective four output conductors 14, which emerge from the motor platform 3 to operate the electric motor 2 via a mains connection 11 in the second operating voltage 5.

The right side of FIG. 10 again shows the motor winding interconnection 1 according to the left side and its four output conductors 14, which are plugged through the motor platform 3. Two respective ones of the four output conductors 14 are short-circuited to each other via a short-circuiting means 9 in order to operate the electric motor 2 via a battery 10 in the first operating voltage 4.

It should be noted that the motor platform 3 may be configured as a circuit board, which has the individual coil 8 and fixed connections on the side facing the electric motor 2 and on the other side correspondingly the output conductors 14 emerge, which are short-circuited via a first or second insertion disk 12 or 13.

The invention claimed is:

1. An electric motor with a motor winding interconnection for operating an electrosurgical instrument with exactly one motor platform, which is provided and configured to operate the motor at a first operating voltage and at a second operating voltage different from the first operating voltage, and a circuit is provided on the motor platform, which is formed in each case by three phases with in each case one phase coil each, and at least one phase coil is formed from N>1 interconnected individual coils, wherein, in the first operating voltage, the N individual coils of each phase coil are connected in parallel and in the second operating voltage, the N individual coils of each phase coil are connected in series, and the switching between the first and second operating voltages via at least one short-circuiting means per phase coil is provided, wherein the at least one short-circuiting means is configured as a passive component that short-circuits the respective interconnected individual coils to connect the individual coils in parallel for the first operating voltage or in series for the second operating voltage, and wherein the motor platform is provided and designed in such a way that the motor characteristic and the characteristic values of the motor are identical during operation in the first and second operating voltages.

2. The electric motor according to claim 1, wherein each phase coil has individual coils and the first operating voltage for operating the motor with a battery is in a ratio of 1/N to the second operating voltage for operating the motor via a mains connection.

3. The electric motor according to claim 1, wherein the first operating voltage and the second operating voltage are in a ratio of ⅓.

4. The electric motor according to claim 1, wherein the at least one short-circuiting means is mounted on a first insertion disk, with which the N individual coils are short-circuited or with which connections between the N individual coils are interrupted in such a way that the N individual coils are connected in parallel with each other in order to operate the motor at the first operating voltage.

5. The electric motor according to claim 4, wherein the at least one short-circuiting means is mounted on a second insertion disk, with which connections between the N individual coils are interrupted or with which the N individual coils are short-circuited in such a way that the N individual coils are connected in series with each other in order to operate the motor at the second operating voltage.

6. The electric motor according to claim 5, wherein the first insertion disk is provided and configured to be inserted between the motor and the battery and the second insertion disk is provided and configured to be inserted between the motor and the mains connection.

7. The electric motor according to claim 5, wherein the first insertion disk is provided and configured to be inserted between the motor and the battery or the second insertion disk is provided and configured to be inserted between the motor and the mains connection.

8. The electric motor according to claim 1, wherein the motor platform has four output conductors per phase, which are directed towards the battery or the mains connection and can be plugged into the short-circuiting means.

9. A motor platform, which carries an entire motor winding interconnection for operating an electrosurgical instrument, comprises a circuit, which is formed by three phases with one phase coil each, and at least one phase coil is formed from N>1 interconnected individual coils, wherein, in the first operating voltage, the N individual coils of each phase coil are connected in parallel and in the second operating voltage, the N individual coils of each phase coil are connected in series, and switching between the first and second operating voltages is provided via at least one short-circuiting means per phase coil, wherein the at least one short-circuiting means is configured as a passive component that short-circuits the respective interconnected individual coils to connect the individual coils in parallel for the first operating voltage or in series for the second operating voltage, and wherein the motor platform is provided and designed in such a way that the motor characteristic and the characteristic values of the motor are identical during operation in the first and second operating voltages, which are different from each other.

10. A surgical instrument comprising the electric motor according to claim 1.

11. A system comprising the electric motor according to claim 1, wherein the electric motor is provided and adapted to be driven by two different voltage sources.

\* \* \* \* \*